United States Patent
Culbert (10) Patent No.: US 9,668,676 B2
(45) Date of Patent: Jun. 6, 2017

(54) USER IDENTIFICATION SYSTEM BASED ON PLETHYSMOGRAPHY

(71) Applicant: Apple Inc., Cupertino, CA (US)

(72) Inventor: Daniel J. Culbert, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/038,419

(22) PCT Filed: Dec. 30, 2013

(86) PCT No.: PCT/US2013/078379
§ 371 (c)(1),
(2) Date: May 20, 2016

(87) PCT Pub. No.: WO2015/102588
PCT Pub. Date: Jul. 9, 2015

(65) Prior Publication Data
US 2016/0296142 A1    Oct. 13, 2016

(51) Int. Cl.
*A61B 5/117*    (2016.01)
*A61B 5/00*    (2006.01)
(Continued)

(52) U.S. Cl.
CPC ............ *A61B 5/117* (2013.01); *A61B 5/0205* (2013.01); *A61B 5/02416* (2013.01);
(Continued)

(58) Field of Classification Search
CPC ... A61B 5/117; A61B 5/0205; A61B 5/02416; A61B 5/14551; A61B 5/6824;
(Continued)

(56) References Cited

U.S. PATENT DOCUMENTS 5,483,261 A    1/1996    Yasutake
5,488,204 A    1/1996    Mead et al.
(Continued)

FOREIGN PATENT DOCUMENTS

EP    2 290 583 A1    3/2011
EP    2 698 686 A2    2/2014
(Continued)

OTHER PUBLICATIONS

Zheng, N. et al. (Oct. 17, 2011) "An Efficient User Verification System via Mouse Movements," Computer and Communications Security, ACM, 2 Penn Plaza, New York, NY, USA, pp. 139-150, XP058006047, DOI: 10.1145/2046707.2046725 ISBN: 978-1-4503-0948-6.
(Continued)

*Primary Examiner* — Leon Flores
(74) *Attorney, Agent, or Firm* — Morrison & Foerster LLP (57) ABSTRACT

A light emitter and light sensor pair can be used to determine one or more characteristics of a user's vasculature. For example, a pulse oximeter employs a light emitter and a light sensor to measure the percentage of oxygenated blood in a subject. In examples of the present disclosure, light emitters and light sensors can be used to perform biometric identification of a user based on identifying characteristics of the user's vasculature. For example, light information can be obtained at one or more light sensors, and the information can be compared to stored information associated with a user identity. Based on the comparison, the user of the device can be identified as having the user identity.

20 Claims, 9 Drawing Sheets

(51) Int. Cl.
*A61B 5/0205* (2006.01)
*A61B 5/024* (2006.01)
*A61B 5/1455* (2006.01)
*G06F 21/32* (2013.01)
*G06F 3/01* (2006.01)
*G06K 9/00* (2006.01)

(52) U.S. Cl.
CPC ........ *A61B 5/14551* (2013.01); *A61B 5/6824* (2013.01); *A61B 5/6898* (2013.01); *A61B 5/7246* (2013.01); *G06F 3/017* (2013.01); *G06F 21/32* (2013.01); *G06K 9/00885* (2013.01); *A61B 5/02438* (2013.01); *G06K 9/00355* (2013.01); *G06K 2009/00939* (2013.01)

(58) Field of Classification Search
CPC ..... A61B 5/6898; A61B 5/7246; G06F 3/017; G06F 21/32
See application file for complete search history.

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,616,110 | B2 | 11/2009 | Crump et al. |
| 7,663,607 | B2 | 2/2010 | Hotelling et al. |
| 8,170,656 | B2 | 5/2012 | Tan et al. |
| 8,378,811 | B2 | 2/2013 | Crump et al. |
| 8,447,704 | B2 | 5/2013 | Tan et al. |
| 8,479,122 | B2 | 7/2013 | Hotelling et al. |
| 8,618,930 | B2 | 12/2013 | Papadopoulos et al. |
| 8,634,808 | B1* | 1/2014 | Zhong ............... H04M 1/66 340/5.8 |
| 8,963,806 | B1* | 2/2015 | Starner ............. G02B 27/0093 345/7 |
| 2002/0024500 | A1 | 2/2002 | Howard |
| 2006/0197753 | A1 | 9/2006 | Hotelling |
| 2008/0300055 | A1 | 12/2008 | Lutnick et al. |
| 2009/0306487 | A1 | 12/2009 | Crowe et al. |
| 2010/0182126 | A1 | 7/2010 | Martis et al. |
| 2010/0289772 | A1* | 11/2010 | Miller ................. G06F 3/0421 345/175 |
| 2011/0054360 | A1 | 3/2011 | Son et al. |
| 2011/0148568 | A1 | 6/2011 | Lim et al. |
| 2011/0173204 | A1 | 7/2011 | Murillo et al. |
| 2011/0235926 | A1 | 9/2011 | Yokono |
| 2012/0127070 | A1 | 5/2012 | Ryoo et al. |
| 2012/0188158 | A1 | 7/2012 | Tan et al. |
| 2014/0031698 | A1 | 1/2014 | Moon et al. |
| 2014/0155705 | A1 | 6/2014 | Papadopoulos et al. |
| 2014/0282270 | A1 | 9/2014 | Slonneger |
| 2016/0091980 | A1 | 3/2016 | Baranski |

FOREIGN PATENT DOCUMENTS

| | | |
|---|---|---|
| JP | 2000-163031 A | 6/2000 |
| JP | 2002-342033 A | 11/2002 |
| WO | WO-2012/138663 A2 | 10/2012 |
| WO | WO-2015/060856 A1 | 4/2015 |
| WO | WO-2015/119637 A1 | 8/2015 |
| WO | WO-2015/121100 A1 | 8/2015 |
| WO | WO-2016/053459 A1 | 4/2016 |

OTHER PUBLICATIONS

Eisenstein, J. S. et al. (May 2, 2001). "Analysis of Clustering Techniques to Detect Hand Signs," *Intelligent Multimedia, Video and Speech Processing, of 2001 International Symposium,* Piscataway, NJ, USA, IEEE, pp: 259-262.
Final Office Action mailed Mar. 10, 2017, for U.S. Appl. No. 14/616,573, filed Feb. 6, 2015, five pages.
International Search Report mailed Mar. 21, 2016, for PCT Application No. PCT/US2015/042976, filed Jul. 30, 2015, six pages.
International Search Report mailed Nov. 7, 2016, for PCT Application No. PCT/US2016/048582, filed Aug. 25, 2016, six pages.
Non-Final Office Action mailed Jun. 16, 2016, for U.S. Appl. No. 14/616,573, filed Feb. 6, 2015, eleven pages.
Reuss, J.L., et al. (Oct. 23-26, 2002). "Period Domain Analysis in Fetal Pulse Oximetry," Proceedings of the Second Joint EMBS/BMES Conference, Houston, TX, two pages.
U.S. Appl. No. 14/616,573, filed Feb. 6, 2015, entitled, "Motion and Gesture Input From a Wearable Device."
Zhao, S. et al. (Nov. 5, 2014). "Wireless Photoplethysmograph Knuckle Sensor System for Measuring Finger Motions," *2014 International Symposium on Optomechatronic Technologies,* IEEE, p. 205-209, XP032783703.
Lee, S.K. et al. (Apr. 1985). "A Multi-Touch Three Dimensional Touch-Sensitive Tablet," *Proceedings of CHI: ACM Conference on Human Factors in Computing Systems,* pp. 21-25.
Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.
Rubine, D.H. (May 1992). "Combining Gestures and Direct Manipulation," CHI '92, pp. 659-660.
Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

USER IDENTIFICATION SYSTEM BASED ON PLETHYSMOGRAPHY

CROSS-REFERENCE TO RELATED APPLICATION

This application is a National Phase application under 35 U.S.C. §371 of International Application No. PCT/US2013/078379, filed Dec. 30, 2013, the content of which is hereby incorporated by reference in its entirety for all intended purposes.

FIELD OF THE DISCLOSURE

This relates generally to biometric identification.

BACKGROUND OF THE DISCLOSURE

A light emitter and light sensor pair can be used to determine one or more characteristics of a user's vasculature. For example, a pulse oximeter employs a light emitter and a light sensor to measure the percentage of oxygenated blood in a subject.

SUMMARY OF THE DISCLOSURE

In examples of the present disclosure, light emitters and light sensors can be used to perform biometric identification of a user based on identifying characteristics of the user's vasculature. For example, light information can be obtained at one or more light sensors, and the information can be compared to stored information associated with a user identity. Based on the comparison, the user of the device can be identified as having the user identity.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

A light emitter and light sensor pair can be used to determine one or more characteristics of a user's vasculature. For example, a pulse oximeter employs a light emitter and a light sensor to measure the percentage of oxygenated blood in a subject. In examples of the present disclosure, light emitters and light sensors can be used to perform biometric identification of a user based on identifying characteristics of the user's vasculature. For example, light information can be obtained at one or more light sensors, and the information can be compared to stored information associated with a user identity. Based on the comparison, the user of the device can be identified as having the user identity.

Although examples disclosed herein may be described and illustrated herein primarily in terms of an emitter/sensor pair for each wavelength, it should be understood that the examples are not so limited, but are additionally applicable to a single emitter that can emit more than one wavelength and/or a single sensor that can sense more than one wavelength. Additionally, examples may identify a user based on any number of wavelengths, and not just two wavelengths as described herein.

Figure 1:
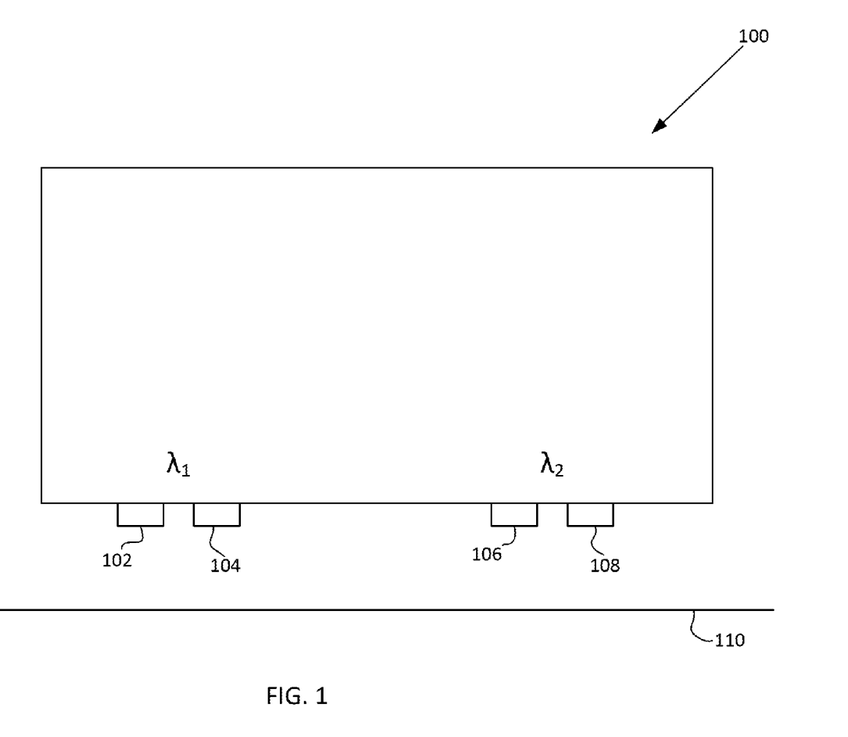
FIG. 1 illustrates an electronic device that performs biometric identification according to examples of the disclosure.

FIG. 1 illustrates an electronic device 100 that performs biometric identification according to examples of the disclosure. A first light emitter 102 and a first light sensor 104 may be co-located on the electronic device. The first light emitter 102 may emit light at a first wavelength $\lambda_1$. A second light emitter 106 and a second light sensor 108 may be co-located on the electronic device. The second light emitter 106 may emit light at a second wavelength $\lambda_2$. During use, the electronic device may be situated proximate to the skin 110 of a user. For example, the electronic device may be strapped to the user's wrist. Each light emitter may emit light towards the user's skin such that a portion of the light is absorbed by the skin, the blood, and/or other parts of the user's body, and an additional portion of the light is reflected back to the co-located light sensor. The light sensor may generate information indicating an amount of light reflected. Such information can be used to determine how much of the light emitted by a co-located light emitter is absorbed by the blood of the user, which can further indicate the volume of blood present in the skin of the user. The volume of blood present in the skin can be a function of several factors, including the cyclical movement of blood to and from the skin and the particular physical characteristics of the vasculature of a user, among other possibilities.

Figure 2A:
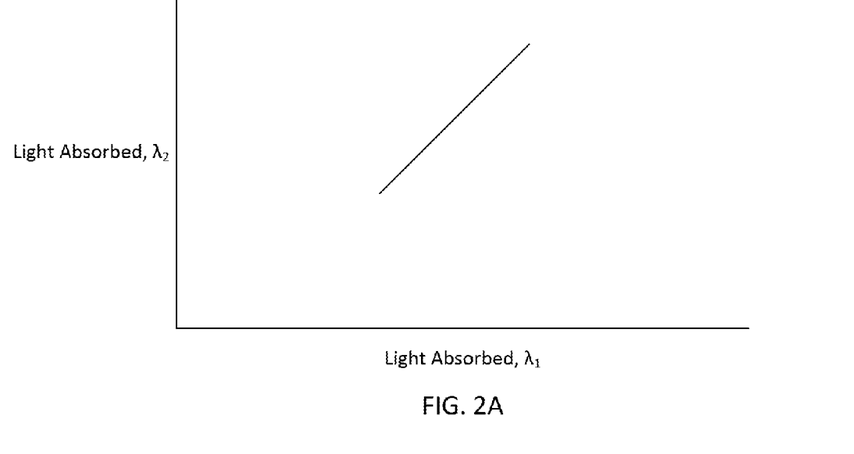
FIG. 2A illustrates a scatterplot showing light absorption by a first light sensor versus light absorption by a second light sensor over a period of time where the user may be stationary according to examples of the disclosure.

FIG. 2A illustrates a scatterplot showing light absorption by the first light sensor ($\lambda_1$) versus light absorption by the second light sensor ($\lambda_2$) over a period of time where the user may be stationary. The light absorption may vary between minimum and maximum values for each wavelength, and the relationship between the absorption of each wavelength may be linear. The shape of the scatterplot may be determined by the cyclical perfusion of blood to the skin of the user and also the physical properties of the user's body, such as the configuration of the vasculature at the skin. Accordingly, the shape of such a scatterplot may vary from user to user. Additionally, the general shape of the scatterplot may be reproducible for a given user if the electronic device is placed at or near the same region of the user's skin. In this way, biometric identification of a user may be possible by comparing the scatterplot to a stored scatterplot for the user using image and/or pattern matching techniques and classification known in the art.

Figure 2B:
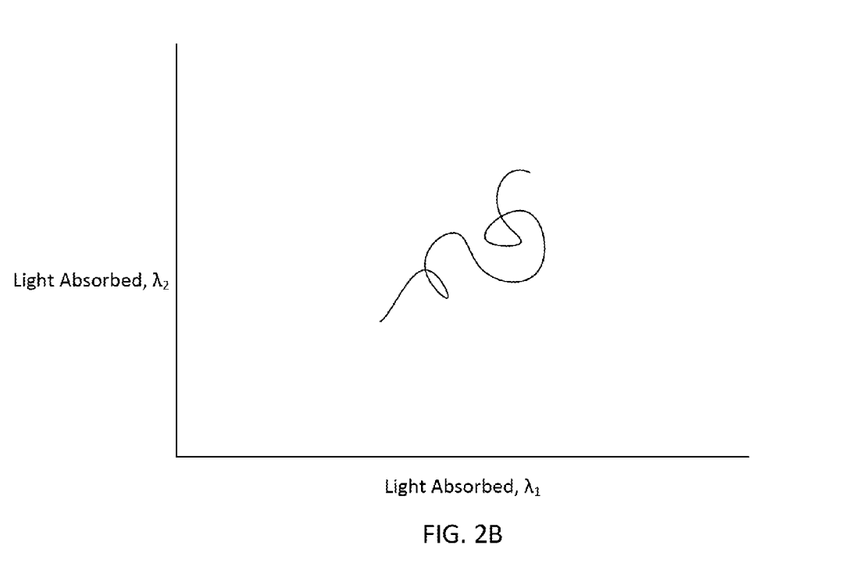
FIG. 2B illustrates a scatterplot showing light absorption by a first light sensor versus light absorption by a second light sensor over a period of time where the user may be moving according to examples of the disclosure.

FIG. 2B illustrates a scatterplot showing light absorption by the first light sensor ($\lambda_1$) versus light absorption by the second light sensor ($\lambda_2$) over a period of time where the user may be moving. Movement may cause the vasculature of the skin to expand and contract, which can affect light absorption in each wavelength differently, as shown in FIG. 2B. Moreover, the variation from user to user can be more pronounced than in the case where the user remains stationary. Here, the general shape of the scatterplot may be reproducible for a given user if the electronic device is placed at or near the same region of the user's skin and if the user moves in the same way. Accordingly, additional sensors of the electronic device may be used to determine that a user has moved the electronic device in a certain way and/or to determine that the user has performed a motion gesture during a time period. Then, the light absorption information received during the time period may be compared to stored light absorption information to perform biometric identification of the user.

Figure 3:
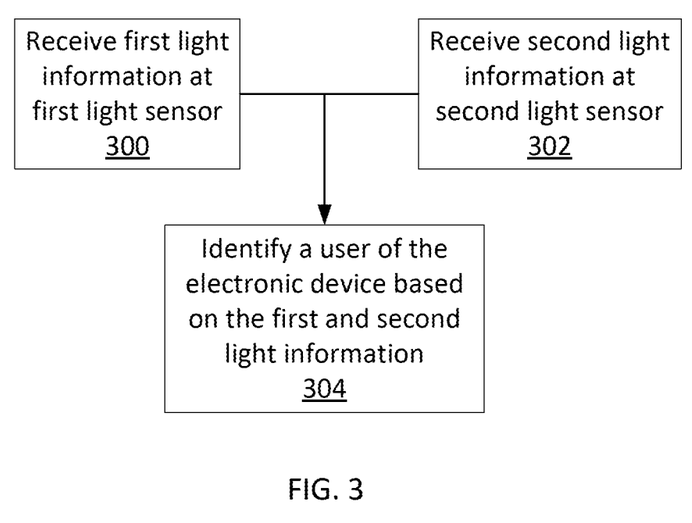
FIG. 3 illustrates an exemplary method of identifying a user of an electronic device based on light information according to examples of the disclosure.

FIG. 3 illustrates an exemplary method of identifying a user of an electronic device based on light information. First light information may be received at a first light sensor (300). The first light sensor may be co-located with a first light emitter, as illustrated in FIG. 1. In some examples, the first light emitter may emit light at a first wavelength, the light may travel to the skin of a user, and a portion of the light may reflect to the first light sensor. Accordingly, the first light information may indicate an amount of light of the first wavelength that has been reflected by the skin, blood, and/or vasculature of the user, among other possibilities. In some examples, the first light information may indicate an amount of light of the first wavelength that has been absorbed by the skin, blood, and/or vasculature of the user. Similarly, second light information may be received at a second light sensor (302). The second light sensor may be co-located with a second light emitter, and the second light emitter may emit light at a second wavelength, different from the first wavelength.

The light emitters may produce light in ranges corresponding to infrared (IR), green, amber, blue, and/or red light, among other possibilities. Additionally, the light sensors may be configured to sense light having certain wavelengths more powerfully than light having other wavelengths. For example, if the first light emitter emits light having a wavelength in the IR range, then the first light sensor may be configured to sense light in the IR range more powerfully than light in the green range. That is, the incidence of light in the IR range may produce a stronger response in the first light sensor than the incidence of light in the green range. In this way, the first light sensor can be configured so as to sense the light produced by the first light emitter more powerfully than the light produced by the second light emitter, for example.

In some examples, a light emitter may be a light emitting diode (LED) and a light sensor may be a photodiode. The light information may include information produced by the photodiode. For example, the light information may include a voltage reading that corresponds to light absorbed by the photodiode. In some examples, the light information may include some transformation of raw data produced by the photodiode.

A user of the electronic device may be identified based on the first and second light information (304). In some examples, the first and second light information may be compared to stored light information associated with a user identity. The received light information may be determined to match the stored light information, and based on the determination the user of the electronic device may be identified as having the user identity.

In some examples, the first and second light information may be arranged in a scatterplot. That is, data points of the first and second light information may be paired based on the collection times of the data points, each data point of the first light information being paired with a data point of the second light information. Examples of such scatterplots are illustrated in FIGS. 2A and 2B. A scatterplot of received light information may be compared to a stored scatterplot of light information using image and/or pattern matching techniques known in the art. A determination that the received light information is similar to the stored light information may be based on such a comparison.

Figure 4:
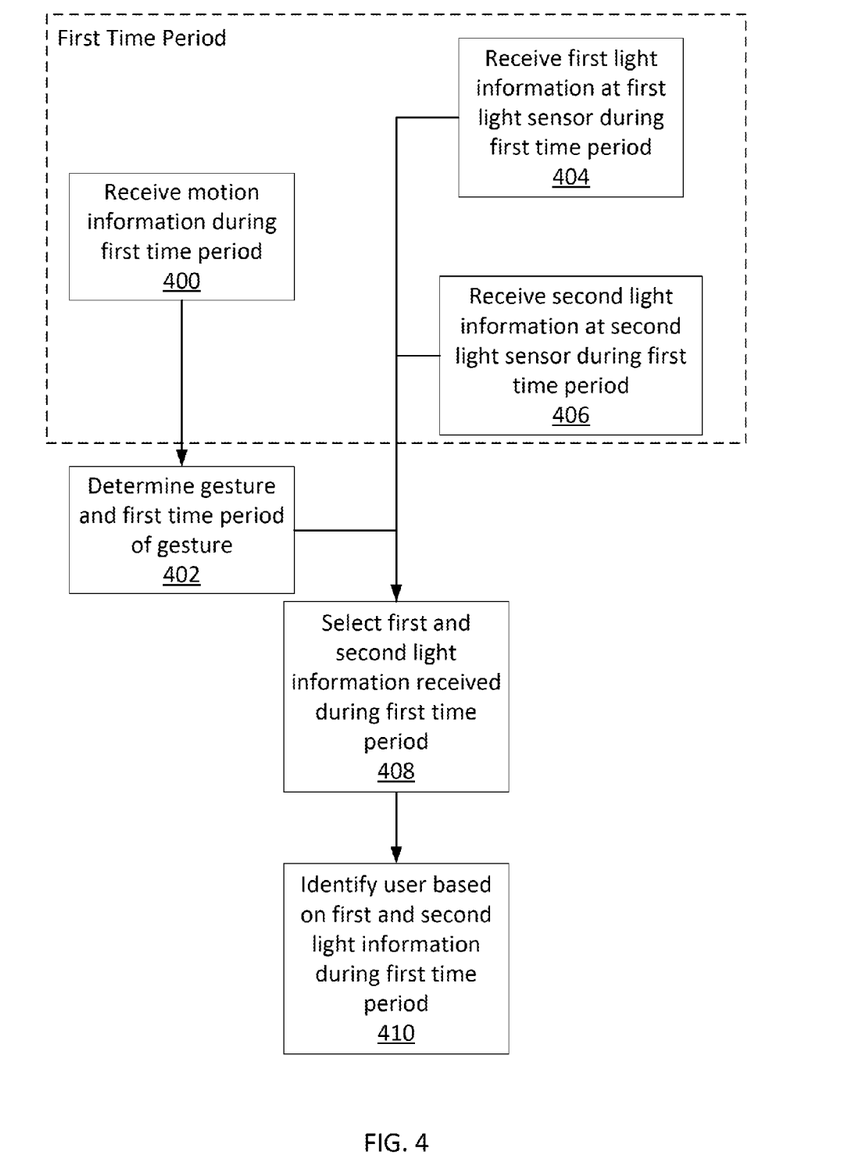
FIG. 4 illustrates an exemplary method of identifying a user of an electronic device based on light information and motion information according to examples of the disclosure.

FIG. 4 illustrates an exemplary method of identifying a user of an electronic device based on light information and motion information. Motion information and first and second light information may be received during a first time period (400, 404, 406). Motion information may be received from one or more sensors of the electronic device, such as an accelerometer, gyroscope, altimeter, barometer, Global Positioning System (GPS), and/or magnetometer, among other possibilities. Such motion may be produced by the movement of a user of the electronic device. For example, the electronic device may be held in the user's hand or strapped to the user's wrist, among other possibilities, and the movements of the user's body can thereby cause movement of the electronic device.

A gesture and a first time period of the gesture may be determined based on the motion information (402). Stored gesture information and/or one or more heuristics may be used to determine a gesture from the motion information. For example, motion information may indicate that the user rapidly moved a hand from her waist to the side of her head, and such a motion can be recognized as a gesture. More specifically, the gesture may be recognized as a gesture associated with the identification process. Additionally, the first time period of the identification gesture may be determined. That is, once the gesture is recognized from the motion information, an initiation time and a finish time of the gesture can be determined.

The first and second light information received during the first time period may be selected based on the determination of the gesture and the first time period of the gesture (408). Once the gesture is recognized and the time period of the gesture is determined, the first and second light information received during that time period may be selected for use in identifying the user (410) as described above.

Figure 5:
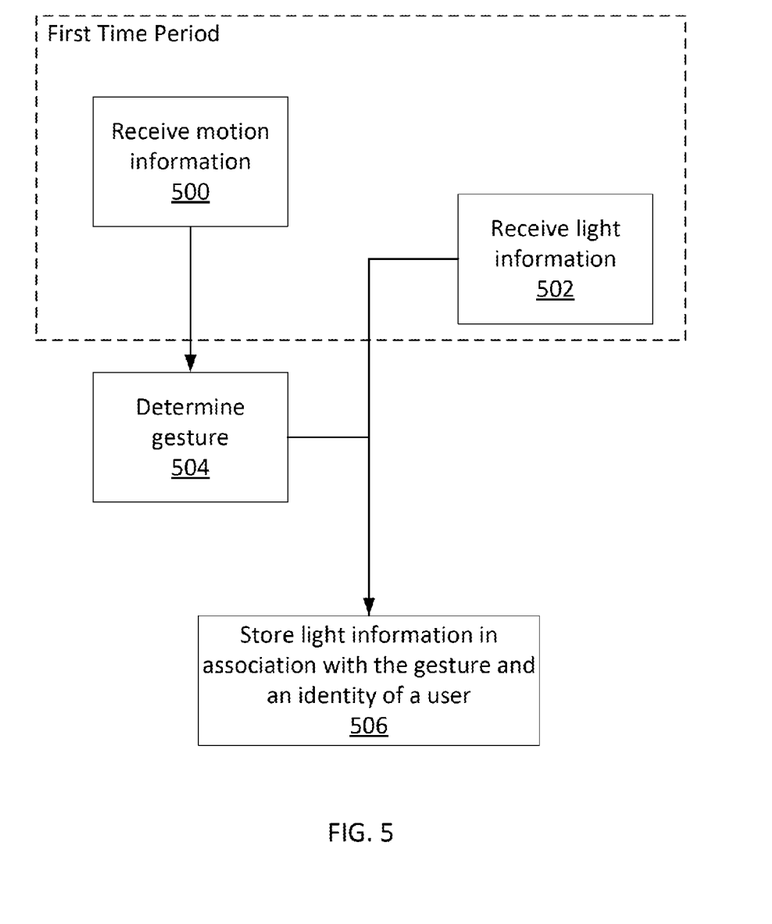
FIG. 5 illustrates a method of storing identifying light information to be used in identification of a user at a later time according to examples of the disclosure.

FIG. 5 illustrates a method of storing identifying light information to be used in identification of a user at a later time. Motion information and light information may be received during a first time period (500, 502). A gesture may be determined from the motion information (504). Then, the light information may be stored in association with the determined identifying gesture and an identity of a user of the electronic device. This stored light information may be used to later identify the user of the electronic device as described above with reference to FIGS. 3 and 4.

In some examples, the identification of a user may be used to enable one or more features of the electronic device. For example, the electronic device may allow a user to access banking information if the user has been properly identified. Additionally or alternatively, identifying a user of the electronic device can include determining that the current user of the electronic device does not have an identity authorized to use the device. For example, the received light information may be compared to stored identifying light information associated with a user identity, and it may be determined that the received light information is not a match. As a result, access to the device may be disabled and/or contents of the device may be deleted. In such a case, the electronic device may not determine a user identity of the user of the device; rather, the electronic device may determine that the user of the device does not have an identity authorized to use the device. This can also be used for automatic user switching. The device may switch to a new mode, user interface (UI), and/or data, depending on which user is identified. It can also be used for enhanced security for peripheral units. For example, an additional electronic device may be associated, connected (wirelessly or otherwise), and/or paired with the electronic device, and the additional electronic device can be configured to only operate if the electronic device with biometric information is present and the identity of the authorized user is currently detected.

The examples discussed above can be implemented in one or more Application Programming Interfaces (APIs). An API is an interface implemented by a program code component or hardware component (hereinafter "API-implementing component") that allows a different program code component or hardware component (hereinafter "API-calling component") to access and use one or more functions, methods, procedures, data structures, classes, and/or other services provided by the API-implementing component. An API can define one or more parameters that are passed between the API-calling component and the API-implementing component.

The above-described features can be implemented as part of an application program interface (API) that can allow it to be incorporated into different applications (e.g., spreadsheet apps) utilizing touch input as an input mechanism. An API can allow a developer of an API-calling component (which may be a third party developer) to leverage specified features, such as those described above, provided by an API-implementing component. There may be one API-calling component or there may be more than one such component. An API can be a source code interface that a computer system or program library provides in order to support requests for services from an application. An operating system (OS) can have multiple APIs to allow applications running on the OS to call one or more of those APIs, and a service (such as a program library) can have multiple APIs to allow an application that uses the service to call one or more of those APIs. An API can be specified in terms of a programming language that can be interpreted or compiled when an application is built.

In some examples, the API-implementing component may provide more than one API, each providing a different view of the functionality implemented by the API-implementing component, or with different aspects that access different aspects of the functionality implemented by the API-implementing component. For example, one API of an API-implementing component can provide a first set of functions and can be exposed to third party developers, and another API of the API-implementing component can be hidden (not exposed) and provide a subset of the first set of functions and also provide another set of functions, such as testing or debugging functions which are not in the first set of functions. In other examples the API-implementing component may itself call one or more other components via an underlying API and thus be both an API-calling component and an API-implementing component.

An API defines the language and parameters that API-calling components use when accessing and using specified features of the API-implementing component. For example, an API-calling component accesses the specified features of the API-implementing component through one or more API calls or invocations (embodied for example by function or method calls) exposed by the API and passes data and control information using parameters via the API calls or invocations. The API-implementing component may return a value through the API in response to an API call from an API-calling component. While the API defines the syntax and result of an API call (e.g., how to invoke the API call and what the API call does), the API may not reveal how the API call accomplishes the function specified by the API call. Various API calls are transferred via the one or more application programming interfaces between the calling (API-calling component) and an API-implementing component. Transferring the API calls may include issuing, initiating, invoking, calling, receiving, returning, or responding to the function calls or messages; in other words, transferring can describe actions by either of the API-calling component or the API-implementing component. The function calls or other invocations of the API may send or receive one or more parameters through a parameter list or other structure. A parameter can be a constant, key, data structure, object, object class, variable, data type, pointer, array, list or a pointer to a function or method or another way to reference a data or other item to be passed via the API.

Furthermore, data types or classes may be provided by the API and implemented by the API-implementing component. Thus, the API-calling component may declare variables, use pointers to, use or instantiate constant values of such types or classes by using definitions provided in the API.

Generally, an API can be used to access a service or data provided by the API-implementing component or to initiate performance of an operation or computation provided by the API-implementing component. By way of example, the API-implementing component and the API-calling component may each be any one of an operating system, a library, a device driver, an API, an application program, or other module (it should be understood that the API-implementing component and the API-calling component may be the same or different type of module from each other). API-implementing components may in some cases be embodied at least in part in firmware, microcode, or other hardware logic. In some examples, an API may allow a client program to use the services provided by a Software Development Kit (SDK) library. In other examples an application or other client program may use an API provided by an Application Framework. In these examples the application or client program may incorporate calls to functions or methods provided by the SDK and provided by the API or use data types or objects defined in the SDK and provided by the API. An Application Framework may in these examples provide a main event loop for a program that responds to various events defined by the Framework. The API allows the application to specify the events and the responses to the events using the Application Framework. In some implementations, an API call can report to an application the capabilities or state of a hardware device, including those related to aspects such as input capabilities and state, output capabilities and state, processing capability, power state, storage capacity and state, communications capability, etc., and the API may be implemented in part by firmware, microcode, or other low level logic that executes in part on the hardware component.

The API-calling component may be a local component (i.e., on the same data processing system as the API-implementing component) or a remote component (i.e., on a different data processing system from the API-implementing component) that communicates with the API-implementing component through the API over a network. It should be understood that an API-implementing component may also act as an API-calling component (i.e., it may make API calls to an API exposed by a different API-implementing component) and an API-calling component may also act as an API-implementing component by implementing an API that is exposed to a different API-calling component.

The API may allow multiple API-calling components written in different programming languages to communicate with the API-implementing component (thus the API may include features for translating calls and returns between the API-implementing component and the API-calling component); however the API may be implemented in terms of a specific programming language. An API-calling component can, in one example, call APIs from different providers such as a set of APIs from an OS provider and another set of APIs from a plug-in provider and another set of APIs from another provider (e.g. the provider of a software library) or creator of the another set of APIs.

Figure 6:
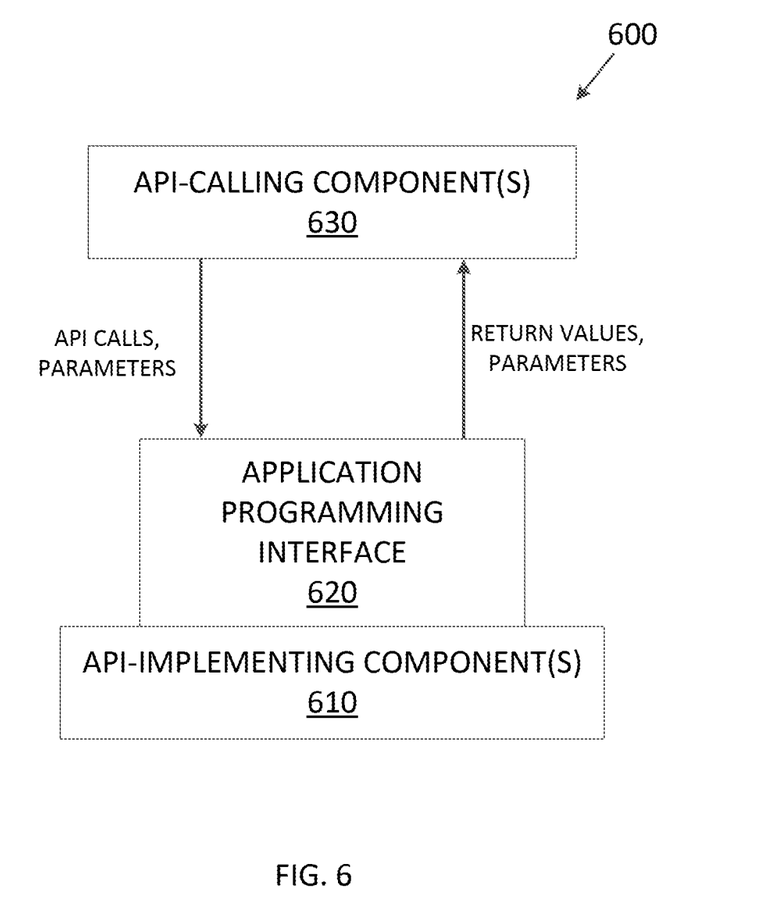
FIG. 6 is a block diagram illustrating an exemplary API architecture, which may be used in some examples of the disclosure.

FIG. 6 is a block diagram illustrating an exemplary API architecture, which may be used in some examples of the disclosure. As shown in FIG. 6, the API architecture 600 includes the API-implementing component 610 (e.g., an operating system, a library, a device driver, an API, an application program, software or other module) that implements the API 620. The API 620 specifies one or more functions, methods, classes, objects, protocols, data structures, formats and/or other features of the API-implementing component that may be used by the API-calling component 630. The API 620 can specify at least one calling convention that specifies how a function in the API-implementing component receives parameters from the API-calling component and how the function returns a result to the API-calling component. The API-calling component 630 (e.g., an operating system, a library, a device driver, an API, an application program, software or other module), makes API calls through the API 620 to access and use the features of the API-implementing component 610 that are specified by the API 620. The API-implementing component 610 may return a value through the API 620 to the API-calling component 630 in response to an API call.

It will be appreciated that the API-implementing component 610 may include additional functions, methods, classes, data structures, and/or other features that are not specified through the API 620 and are not available to the API-calling component 630. It should be understood that the API-calling component 630 may be on the same system as the API-implementing component 610 or may be located remotely and accesses the API-implementing component 610 using the API 620 over a network. While FIG. 6 illustrates a single API-calling component 630 interacting with the API 620, it should be understood that other API-calling components, which may be written in different languages (or the same language) than the API-calling component 630, may use the API 620.

The API-implementing component 610, the API 620, and the API-calling component 630 may be stored in a non-transitory machine-readable storage medium, which includes any mechanism for storing information in a form readable by a machine (e.g., a computer or other data processing system). For example, a machine-readable medium includes magnetic disks, optical disks, random access memory; read only memory, flash memory devices, etc.

Figure 7:
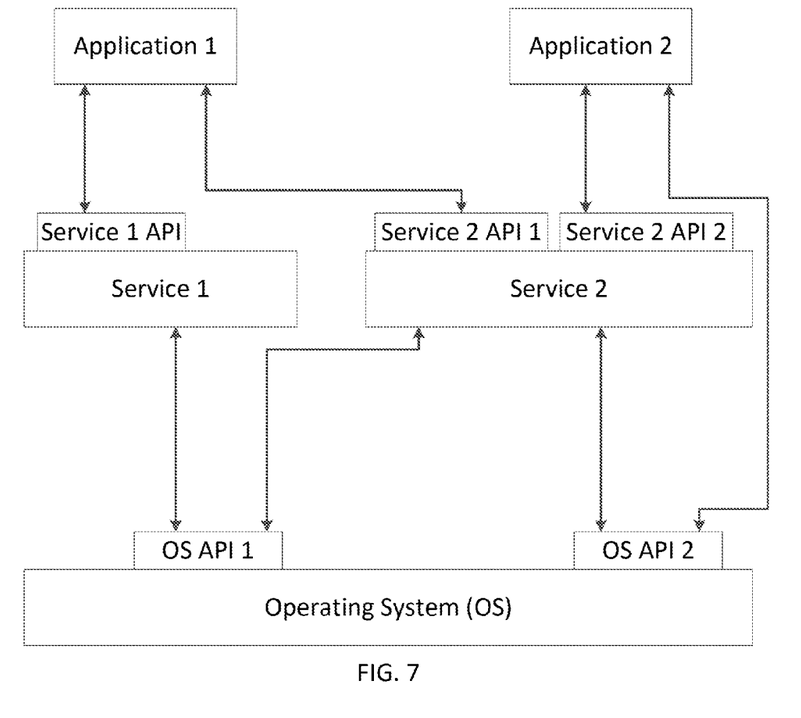
FIG. 7 illustrates an exemplary software stack of an API according to examples of the disclosure.

In the exemplary software stack shown in FIG. 7, applications can make calls to Services A or B using several Service APIs and to Operating System (OS) using several OS APIs. Services A and B can make calls to OS using several OS APIs.

Note that the Service 2 has two APIs, one of which (Service 2 API 1) receives calls from and returns values to Application 1 and the other (Service 2 API 2) receives calls from and returns values to Application 2. Service 1 (which can be, for example, a software library) makes calls to and receives returned values from OS API 1, and Service 2 (which can be, for example, a software library) makes calls to and receives returned values from both OS API 1 and OS API 2. Application 2 makes calls to and receives returned values from OS API 2.

Figure 8:
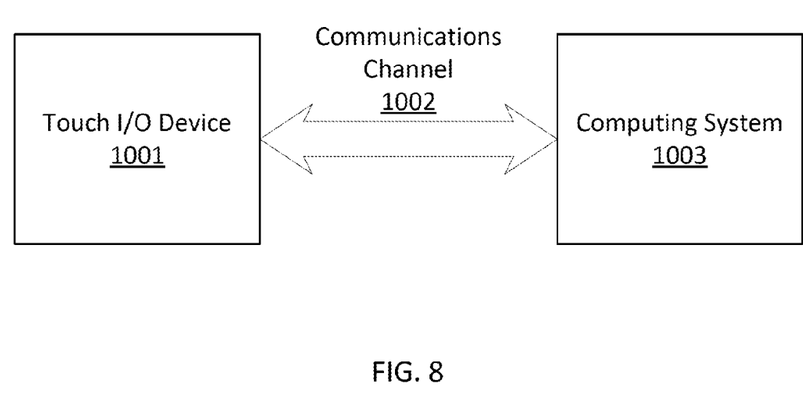
FIG. 8 is a block diagram illustrating exemplary interactions between the touch screen and other components of the device according to examples of the disclosure.

FIG. 8 is a block diagram illustrating exemplary interactions between the touch screen and the other components of the device. Described examples may include touch I/O device 1001 that can receive touch input for interacting with computing system 1003 via wired or wireless communication channel 1002. Touch I/O device 1001 may be used to provide user input to computing system 1003 in lieu of or in combination with other input devices such as a keyboard, mouse, etc. One or more touch I/O devices 1001 may be used for providing user input to computing system 1003. Touch I/O device 1001 may be an integral part of computing system 1003 (e.g., touch screen on a smartphone or a tablet PC) or may be separate from computing system 1003.

Touch I/O device 1001 may include a touch sensing panel which is wholly or partially transparent, semitransparent, non-transparent, opaque or any combination thereof. Touch I/O device 1001 may be embodied as a touch screen, touch pad, a touch screen functioning as a touch pad (e.g., a touch screen replacing the touchpad of a laptop), a touch screen or touchpad combined or incorporated with any other input device (e.g., a touch screen or touchpad disposed on a keyboard) or any multi-dimensional object having a touch sensing surface for receiving touch input.

In one example, touch I/O device 1001 embodied as a touch screen may include a transparent and/or semitransparent touch sensing panel partially or wholly positioned over at least a portion of a display. According to this example, touch I/O device 1001 functions to display graphical data transmitted from computing system 1003 (and/or another source) and also functions to receive user input. In other examples, touch I/O device 1001 may be embodied as an integrated touch screen where touch sensing components/devices are integral with display components/devices. In still other examples a touch screen may be used as a supplemental or additional display screen for displaying supplemental or the same graphical data as a primary display and to receive touch input.

Touch I/O device 1001 may be configured to detect the location of one or more touches or near touches on device 1001 based on capacitive, resistive, optical, acoustic, inductive, mechanical, chemical measurements, or any phenomena that can be measured with respect to the occurrences of the one or more touches or near touches in proximity to device 1001. Software, hardware, firmware or any combination thereof may be used to process the measurements of the detected touches to identify and track one or more gestures. A gesture may correspond to stationary or non-stationary, single or multiple, touches or near touches on touch I/O device 1001. A gesture may be performed by moving one or more fingers or other objects in a particular manner on touch I/O device 1001 such as tapping, pressing, rocking, scrubbing, twisting, changing orientation, pressing with varying pressure and the like at essentially the same time, contiguously, or consecutively. A gesture may be characterized by, but is not limited to a pinching, sliding, swiping, rotating, flexing, dragging, or tapping motion between or with any other finger or fingers. A single gesture may be performed with one or more hands, by one or more users, or any combination thereof.

Computing system 1003 may drive a display with graphical data to display a graphical user interface (GUI). The GUI may be configured to receive touch input via touch I/O device 1001. Embodied as a touch screen, touch I/O device 1001 may display the GUI. Alternatively, the GUI may be displayed on a display separate from touch I/O device 1001. The GUI may include graphical elements displayed at particular locations within the interface. Graphical elements may include but are not limited to a variety of displayed virtual input devices including virtual scroll wheels, a virtual keyboard, virtual knobs, virtual buttons, any virtual UI, and the like. A user may perform gestures at one or more particular locations on touch I/O device 1001 which may be associated with the graphical elements of the GUI. In other examples, the user may perform gestures at one or more locations that are independent of the locations of graphical elements of the GUI. Gestures performed on touch I/O device 1001 may directly or indirectly manipulate, control, modify, move, actuate, initiate or generally affect graphical elements such as cursors, icons, media files, lists, text, all or portions of images, or the like within the GUI. For instance, in the case of a touch screen, a user may directly interact with a graphical element by performing a gesture over the graphical element on the touch screen. Alternatively, a touch pad generally provides indirect interaction. Gestures may also affect non-displayed GUI elements (e.g., causing user interfaces to appear) or may affect other actions within computing system 1003 (e.g., affect a state or mode of a GUI, application, or operating system). Gestures may or may not be performed on touch I/O device 1001 in conjunction with a displayed cursor. For instance, in the case in which gestures are performed on a touchpad, a cursor (or pointer) may be displayed on a display screen or touch screen and the cursor may be controlled via touch input on the touchpad to interact with graphical objects on the display screen. In other examples in which gestures are performed directly on a touch screen, a user may interact directly with objects on the touch screen, with or without a cursor or pointer being displayed on the touch screen.

Feedback may be provided to the user via communication channel 1002 in response to or based on the touch or near touches on touch I/O device 1001. Feedback may be transmitted optically, mechanically, electrically, olfactory, acoustically, or the like or any combination thereof and in a variable or non-variable manner.

Figure 9:
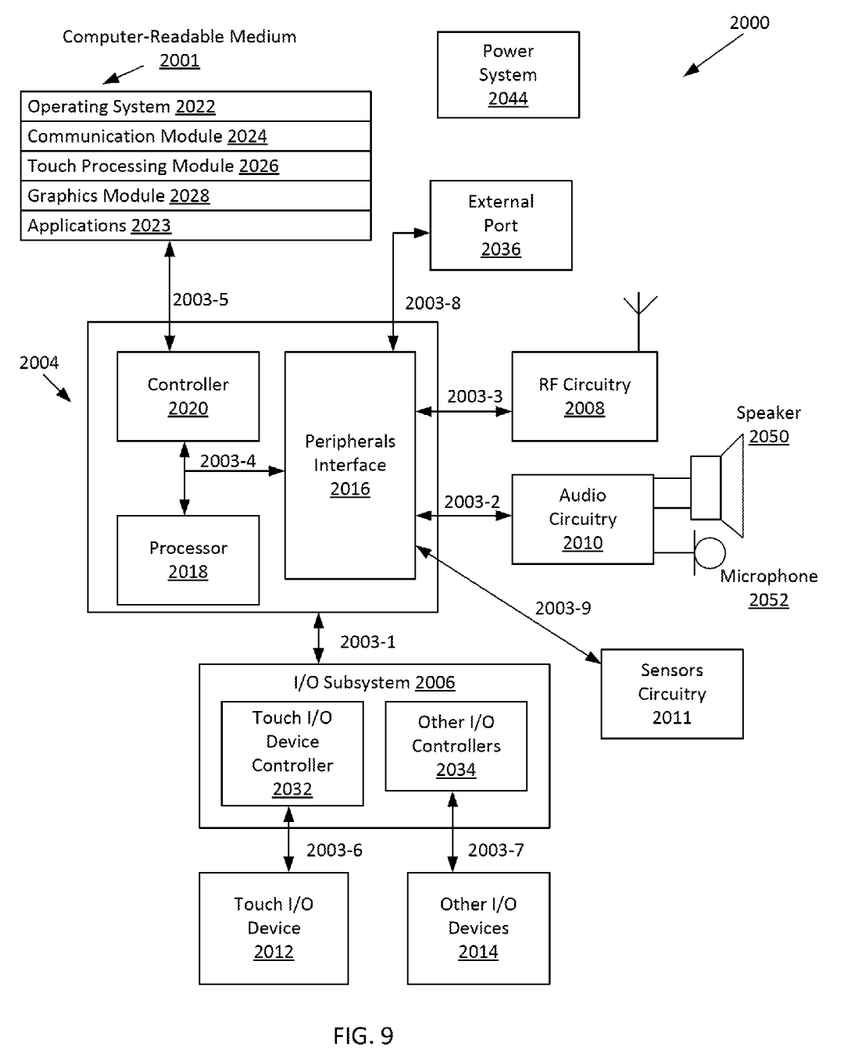
FIG. 9 is a block diagram illustrating an example of a system architecture that may be embodied within any portable or non-portable device according to examples of the disclosure.

Attention is now directed towards examples of a system architecture that may be embodied within any portable or non-portable device including but not limited to a communication device (e.g. mobile phone, smart phone), a multimedia device (e.g., MP3 player, TV, radio), a portable or handheld computer (e.g., tablet, netbook, laptop), a desktop computer, an All-In-One desktop, a peripheral device, or any other system or device adaptable to the inclusion of system architecture 2000, including combinations of two or more of these types of devices. FIG. 9 is a block diagram of one example of system 2000 that generally includes one or more computer-readable mediums 2001, processing system 2004, I/O subsystem 2006, radio frequency (RF) circuitry 2008, audio circuitry 2010, and sensors circuitry 2011. These components may be coupled by one or more communication buses or signal lines 2003.

It should be apparent that the architecture shown in FIG. 9 is only one example architecture of system 2000, and that system 2000 could have more or fewer components than shown, or a different configuration of components. The various components shown in FIG. 9 can be implemented in hardware, software, firmware or any combination thereof, including one or more signal processing and/or application specific integrated circuits.

RF circuitry 2008 is used to send and receive information over a wireless link or network to one or more other devices and includes well-known circuitry for performing this function. RF circuitry 2008 and audio circuitry 2010 are coupled to processing system 2004 via peripherals interface 2016. Interface 2016 includes various known components for establishing and maintaining communication between peripherals and processing system 2004. Audio circuitry 2010 is coupled to audio speaker 2050 and microphone 2052 and includes known circuitry for processing voice signals received from interface 2016 to enable a user to communicate in real-time with other users. In some examples, audio circuitry 2010 includes a headphone jack (not shown). Sensors circuitry 2011 can be coupled to various sensors including, but not limited to, one or more Light Emitting Diodes (LEDs) or other light emitters, one or more photodiodes or other light sensors, a magnetometer, an accelerometer, a gyroscope, a barometer, a compass, a proximity sensor, a camera, an ambient light sensor, a thermometer, a GPS sensor, and various system sensors which can sense remaining battery life, power consumption, processor speed, CPU load, and the like.

Peripherals interface 2016 couples the input and output peripherals of the system to processor 2018 and computer-readable medium 2001. One or more processors 2018 communicate with one or more computer-readable mediums 2001 via controller 2020. Computer-readable medium 2001 can be any device or medium that can store code and/or data for use by one or more processors 2018. Medium 2001 can include a memory hierarchy, including but not limited to cache, main memory and secondary memory. The memory hierarchy can be implemented using any combination of RAM (e.g., SRAM, DRAM, DDRAM), ROM, FLASH, magnetic and/or optical storage devices, such as disk drives, magnetic tape, CDs (compact disks) and DVDs (digital video discs). Medium 2001 may also include a transmission medium for carrying information-bearing signals indicative of computer instructions or data (with or without a carrier wave upon which the signals are modulated). For example, the transmission medium may include a communications network, including but not limited to the Internet (also referred to as the World Wide Web), intranet(s), Local Area Networks (LANs), Wide Local Area Networks (WLANs), Storage Area Networks (SANs), Metropolitan Area Networks (MAN) and the like.

One or more processors 2018 run various software components stored in medium 2001 to perform various functions for system 2000. In some examples, the software components include operating system 2022, communication module (or set of instructions) 2024, touch processing module (or set of instructions) 2026, graphics module (or set of instructions) 2028, and one or more applications (or set of instructions) 2030. Each of these modules and above noted applications correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules may be combined or otherwise re-arranged in various examples. In some examples, medium 2001 may store a subset of the modules and data structures identified above. Furthermore, medium 2001 may store additional modules and data structures not described above.

Operating system 2022 includes various procedures, sets of instructions, software components and/or drivers for controlling and managing general system tasks (e.g., memory management, storage device control, power management, etc.) and facilitates communication between various hardware and software components.

Communication module 2024 facilitates communication with other devices over one or more external ports 2036 or via RF circuitry 2008 and includes various software components for handling data received from RF circuitry 2008 and/or external port 2036.

Graphics module 2028 includes various known software components for rendering, animating and displaying graphical objects on a display surface. In examples in which touch I/O device 2012 is a touch sensing display (e.g., touch screen), graphics module 2028 includes components for rendering, displaying, and animating objects on the touch sensing display.

One or more applications 2030 can include any applications installed on system 2000, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player, etc.

Touch processing module 2026 includes various software components for performing various tasks associated with touch I/O device 2012 including but not limited to receiving and processing touch input received from I/O device 2012 via touch I/O device controller 2032.

I/O subsystem 2006 is coupled to touch I/O device 2012 and one or more other I/O devices 2014 for controlling or performing various functions. Touch I/O device 2012 communicates with processing system 2004 via touch I/O device controller 2032, which includes various components for processing user touch input (e.g., scanning hardware). One or more other input controllers 2034 receives/sends electrical signals from/to other I/O devices 2014. Other I/O devices 2014 may include physical buttons, dials, slider switches, sticks, keyboards, touch pads, additional display screens, or any combination thereof.

If embodied as a touch screen, touch I/O device 2012 displays visual output to the user in a GUI. The visual output may include text, graphics, video, and any combination thereof. Some or all of the visual output may correspond to user-interface objects. Touch I/O device 2012 forms a touch sensing surface that accepts touch input from the user. Touch I/O device 2012 and touch screen controller 2032 (along with any associated modules and/or sets of instructions in medium 2001) detects and tracks touches or near touches (and any movement or release of the touch) on touch I/O device 2012 and converts the detected touch input into interaction with graphical objects, such as one or more user-interface objects. In the case in which device 2012 is embodied as a touch screen, the user can directly interact with graphical objects that are displayed on the touch screen. Alternatively, in the case in which device 2012 is embodied as a touch device other than a touch screen (e.g., a touch pad), the user may indirectly interact with graphical objects that are displayed on a separate display screen embodied as I/O device 2014.

Touch I/O device 2012 may be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference.

Examples in which touch I/O device 2012 is a touch screen, the touch screen may use LCD (liquid crystal display) technology, LPD (light emitting polymer display) technology, OLED (organic LED), or OEL (organic electro luminescence), although other display technologies may be used in other examples.

Feedback may be provided by touch I/O device 2012 based on the user's touch input as well as a state or states of what is being displayed and/or of the computing system. Feedback may be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

System 2000 also includes power system 2044 for powering the various hardware components and may include a power management system, one or more power sources, a recharging system, a power failure detection circuit, a power converter or inverter, a power status indicator and any other components typically associated with the generation, management and distribution of power in portable devices.

In some examples, peripherals interface 2016, one or more processors 2018, and memory controller 2020 may be implemented on a single chip, such as processing system 2004. In some other examples, they may be implemented on separate chips.

Examples of the disclosure can be advantageous in allowing for an electronic device to automatically identify a user based on biometrics, making use of the electronic device easier, more intuitive, and more secure.

In some examples, a method of an electronic device including a plurality of light sensors and light emitters may be disclosed. The method may include: receiving first light information at a first light sensor co-located with a first light emitter of at least a first wavelength; receiving second light information at a second light sensor co-located with a light emitter of at least a second wavelength; and identifying a user of the electronic device based on the first and second light information. Additionally or alternatively to one or more of the examples described above, the method may further include: receiving motion information of the electronic device; based on the motion information, determining a gesture of the electronic device performed during a first time period; and based on the determination of the gesture, selecting the first and second light information received during the first time period for use in identifying the user of the electronic device. Additionally or alternatively to one or more of the examples described above, identifying the user of the electronic device based on the first and second light information may include comparing the first and second light information to stored light information associated with the gesture. Additionally or alternatively to one or more of the examples described above, the method may further include determining the first time period based on the determination of the gesture, wherein selecting the first and second light information received during the first time period may be based on the determination of the first time period. Additionally or alternatively to one or more of the examples described above, the method may further include: comparing the first and second light information to stored light information associated with a user identity; and determining that the first and second light information matches the stored light information based on the comparison; wherein identifying the user of the electronic device may include identifying the user as having the user identity based on the determination that the first and second light information matches the stored light information associated with the user identity. Additionally or alternatively to one or more of the examples described above, identifying the user of the electronic device may include determining that the user of the electronic device does not have an identity authorized to use the device.

In some examples, a method of an electronic device including a one or more light sensors and light emitters may be disclosed. The method may include: receiving motion information of the electronic device; based on the motion information, determining a gesture of the electronic device performed during a first time period; receiving light information during the first time period; and storing the light information in association with the gesture and an identity of a user of the electronic device.

In some examples, a non-transitory computer readable medium may be disclosed. The computer readable medium may contain instructions that, when executed, perform a method of an electronic device including a plurality of light sensors and light emitters. The method may include: receiving first light information at a first light sensor co-located with a first light emitter of at least a first wavelength; receiving second light information at a second light sensor co-located with a light emitter of at least a second wavelength; and identifying a user of the electronic device based on the first and second light information. Additionally or alternatively to one or more of the examples described above, the method may further include: receiving motion information of the electronic device; based on the motion information, determining a gesture of the electronic device performed during a first time period; and based on the determination of the gesture, selecting the first and second light information received during the first time period for use in identifying the user of the electronic device. Additionally or alternatively to one or more of the examples described above, identifying the user of the electronic device based on the first and second light information may include comparing the first and second light information to stored light information associated with the gesture. Additionally or alternatively to one or more of the examples described above, the method may further include determining the first time period based on the determination of the gesture, wherein selecting the first and second light information received during the first time period may be based on the determination of the first time period. Additionally or alternatively to one or more of the examples described above, the method may further include: comparing the first and second light information to stored light information associated with a user identity; and determining that the first and second light information matches the stored light information based on the comparison; wherein identifying the user of the electronic device may include identifying the user as having the user identity based on the determination that the first and second light information matches the stored light information associated with the user identity. Additionally or alternatively to one or more of the examples described above, identifying the user of the electronic device may include determining that the user of the electronic device does not have an identity authorized to use the device.

In some examples, a non-transitory computer readable medium may be disclosed. The computer readable medium may contain instructions that, when executed, perform a method of an electronic device including a one or more light sensors and light emitters. The method may include: receiving motion information of the electronic device; based on the motion information, determining a gesture of the electronic device performed during a first time period; receiving light information during the first time period; and storing the light information in association with the gesture and an identity of a user of the electronic device.

In some examples, an electronic device may be disclosed. The electronic device may include: a processor to execute instructions; a first light emitter of at least a first wavelength; a second light emitter of at least a second wavelength; a first light sensor co-located with the first light emitter; a second light sensor co-located with the second light emitter; and a memory coupled with the processor to store instructions, which when executed by the processor, cause the processor to perform operations to generate an application programming interface (API) that allows an API-calling component to perform a method comprising: receiving first light information at the first light sensor; receiving second light information at the second light sensor; and identifying a user of the electronic device based on the first and second light information. Additionally or alternatively to one or more of the examples described above, the method may further include: receiving motion information of the electronic device; based on the motion information, determining a gesture of the electronic device performed during a first time period; and based on the determination of the gesture, selecting the first and second light information received during the first time period for use in identifying the user of the electronic device. Additionally or alternatively to one or more of the examples described above, identifying the user of the electronic device based on the first and second light information may include comparing the first and second light information to stored light information associated with the gesture. Additionally or alternatively to one or more of the examples described above, the method may further include determining the first time period based on the determination of the gesture, wherein selecting the first and second light information received during the first time period may be based on the determination of the first time period. Additionally or alternatively to one or more of the examples described above, the method may further include: comparing the first and second light information to stored light information associated with a user identity; and determining that the first and second light information matches the stored light information based on the comparison; wherein identifying the user of the electronic device may include identifying the user as having the user identity based on the determination that the first and second light information matches the stored light information associated with the user identity. Additionally or alternatively to one or more of the examples described above, identifying the user of the electronic device may include determining that the user of the electronic device does not have an identity authorized to use the device.

In some examples, an electronic device may be disclosed. The electronic device may include: a processor to execute instructions; one or more light sensors; one or more light emitters; a memory coupled with the processor to store instructions, which when executed by the processor, cause the processor to perform operations to generate an application programming interface (API) that allows an API-calling component to perform a method comprising: receiving motion information of the electronic device; based on the motion information, determining a gesture of the electronic device performed during a first time period; receiving light information during the first time period; and storing the light information in association with the gesture and an identity of a user of the electronic device.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. A method of an electronic device including a plurality of light sensors and light emitters, the method comprising:
receiving first light information at a first light sensor co-located with a first light emitter of at least a first wavelength, the first light information based on a reflection of light emitted by the first light emitter, wherein receiving the first light information includes receiving a plurality of first light information data points over a plurality of collection times;
receiving second light information at a second light sensor co-located with a second light emitter of at least a second wavelength, different from the first wavelength, the second light information based on a reflection of light emitted by the second light emitter, the second light sensor and the second light emitter separate and distinct from the first light sensor and the first light emitter, respectively,
wherein receiving the second light information includes receiving a plurality of second light information data points over the plurality of collection times;
for each of the plurality of collection times, associating the first information with the collection time to the second information associated with the collection time;
generating a scatterplot using the associations of the first information to the second information with the collection time;
comparing the generated scatterplot to a stored scatterplot;
determining one or more physical characteristics of a vasculature of a user based on the comparison; and
identifying the user of the electronic device based on the one or more physical characteristics of the vasculature.

2. The method of claim 1, further comprising:
receiving motion information of the electronic device;
based on the motion information, determining a gesture of the electronic device performed during a first time period; and
based on the determination of the gesture, selecting the first and second light information received during the first time period for use in identifying the user of the electronic device.

3. The method of claim 2, wherein identifying the user of the electronic device based on the first and second light information includes comparing the first and second light information to stored light information associated with the gesture.

4. The method of claim 2, further comprising:
determining the first time period based on the determination of the gesture, wherein selecting the first and second light information received during the first time period is based on the determination of the first time period.

5. The method of claim 1, further comprising:
comparing the first and second light information to stored light information associated with a user identity; and
determining that the first and second light information matches the stored light information based on the comparison;
wherein identifying the user of the electronic device includes identifying the user as having the user identity based on the determination that the first and second light information matches the stored light information associated with the user identity.

6. The method of claim 1, wherein identifying the user of the electronic device includes determining that the user of the electronic device does not have an identity authorized to use the device.

7. The method of claim 1, further comprising:
receiving motion information of the electronic device from one or more motion sensors;
based on the motion information, determining a gesture of the electronic device performed during a time period;
determining an initiation time and a finish time included in the time period of the gesture; and
storing the light information in association with the gesture and the identity of the user of the electronic device.

8. The method of claim 1, wherein identifying the user includes comparing the scatterplot to a stored light information.

9. The method of claim 1, wherein comparing the scatterplot to the stored light information includes matching a pattern of the scatterplot to a pattern of the stored light information.

10. The method of claim 1, wherein the one or more physical characteristics includes a percentage of oxygenated blood in the user.

11. The method of claim 1, wherein the one or more physical characteristics includes a volume of blood present in a skin of the user.

12. The method of claim 1, further comprising:
comparing the identified user to a user identity; and
allowing the user to access one or more features of the electronic device when the identified user matches the user identity.

13. The method of claim 1, wherein comparing the generated scatterplot to the stored scatterplot includes comparing a shape of the generated scatterplot to a shape of the stored scatterplot.

14. An electronic device, comprising:
a first light emitter configured to emit at least a first wavelength;
a second light emitter configured to emit at least a second wavelength;
a first light sensor co-located with the first light emitter and configured to detect a reflection of light emitted by the first light emitter;

a second light sensor co-located with the second light emitter and configured to detect a reflection of light emitted by the second light emitter; and a processor configured to:
  receive first light information from the first light sensor including receiving a plurality of first light information data points over a plurality of collection times;
  receive second light information at the second light sensor including receiving a plurality of second light information data points over a plurality of collection times;
  for each of the plurality of collection times, associating the first information with the collection time to the second information associated with the collection time;
  generating a scatterplot using the associations of the first information to the second information with the collection time;
  comparing the generated scatterplot to a stored scatterplot;
  determine one or more physical characteristics of a vasculature of a user based on the comparison; and
  identify a user of the electronic device based on the physical characteristics of the vasculature.

15. The electronic device of claim 14, further comprising:
a mechanical sensor configured to receive motion information of the electronic device, wherein the processor is further configured to:
  determine a gesture of the electronic device performed during a first time period based on the motion information, and
  select the first and second light information received during the first time period for use in identifying the user of the electronic device based on the determined gesture.

16. The electronic device of claim 15, wherein the processor is further configured to: compare the first and second light information to stored light information associated with the determined gesture.

17. The electronic device of claim 15, wherein the processor is further configured to:
  determine the first time period based on the determination of the gesture, wherein selecting the first and second light information received during the first time period is based on the determination of the first time period.

18. The electronic device of claim 14, wherein the processor is further configured to:
  compare the first and second light information to stored light information associated with a user identity; and
  determine whether the first and second light information match the stored light information based on the comparison,
  wherein identifying the user of the electronic device includes identifying the user as having the user identity based on the determination that the first and second light information matches the stored light information associated with the user identity.

19. The electronic device of claim 14, wherein the mechanical sensor is one or more of an accelerometer, a gyroscope, an altimeter, a barometer, and a global positioning system.

20. The electronic device of claim 14, wherein one or more of the first light emitter and second light emitter are configured to emit one or more of infrared, green, amber, blue, and red light.

\* \* \* \* \*